United States Patent [19]

Drent

[11] Patent Number: 5,034,368

[45] Date of Patent: Jul. 23, 1991

[54] PROCESS FOR THE PREPARATION OF CARBOXYLIC ACIDS OR ESTERS THEREOF

[75] Inventor: Eit Drent, Amsterdmn, Netherlands

[73] Assignee: Shell Oil Company, Houston, Tex.

[21] Appl. No.: 468,444

[22] Filed: Jan. 22, 1990

Related U.S. Application Data

[62] Division of Ser. No. 192,551, May 11, 1988, Pat. No. 4,902,822.

[30] Foreign Application Priority Data

May 15, 1987 [GB] United Kingdom ............... 8711524

[51] Int. Cl.$^5$ .................. B01J 31/02; B01J 31/22; B01J 31/38
[52] U.S. Cl. ................................ 502/168; 502/171; 502/203; 502/207; 502/213
[58] Field of Search ............... 502/168, 171, 203, 207, 502/213

[56] References Cited

FOREIGN PATENT DOCUMENTS 105704 4/1984 European Pat. Off. .
106379 4/1984 European Pat. Off. .

Primary Examiner—Patrick P. Garvin

[57] ABSTRACT

A process for the preparation of carboxylic acids or of esters thereof by contacting an olefinically unsaturated compound with CO in the presence of water or an alcohol, respectively, and of a catalytic system prepared by combining a ruthenium compound and a compound having a non-coordinating anion of an acid with a $pK_a$ below 0.5; compositions comprising a ruthenium compound and a salt having a non-coordinating anion of an acid with a $pK_a$ below 0.5 are novel.

3 Claims, No Drawings

PROCESS FOR THE PREPARATION OF CARBOXYLIC ACIDS OR ESTERS THEREOF

This is a division of application Ser. No. 07/192,551, filed May 11, 1988 and now U.S. Pat. No. 4,902,822.

This invention relates to a process for the preparation of carboxylic acids or of esters thereof. The invention also relates to a novel composition.

BACKGROUND OF THE INVENTION

U.S. patent specification No. 3,168,553 discloses a process in which olefins are carbonylated in the presence of a catalyst complex comprising a trialkyphosphine together with cobalt, ruthenium, rhodium or iridium. However, this process requires the use of high pressure, and its selectivity towards the desired product is often unsatisfactory. For instance, the carbonylation of ethylene in the presence of ethanol and a $CO_2(CO)_8$ catalyst leads to the formation not only of ethyl propionate, but also of large quantities of by-products, such as diethyl ketone and acetaldehyde.

SUMMARY OF THE INVENTION

It has now surprisingly been found that carboxylic acids or esters thereof are formed at a high selectivity in a relatively low pressure carbonylation process which comprises contacting an olefinically unsaturated compound with carbon monoxide in the presence of water or an alcohol, respectively, and in the presence of a ruthenium compound and a specified compound having a non-coordinating anion of an acid of low pKa.

Accordingly, this invention provides a process for the preparation of carboxylic acids and carboxylic acid esters which process comprises contacting an olefinically unsaturated compound with carbon monoxide in the presence of (i) water or an alcohol and (ii) a catalytic system which comprises a combination of the following components:

component (a)—a ruthenium compound, and
component (b)—a compound having a non-coordinating anion of an acid with a $pK_a$ below 0.5, as measured at 25° C. in aqueous solution.

The selectivity ("S") of a given reaction to the production of a certain compound, expressed in a percentage, is defined herein by the formula $S = 100 \times (c/d)$, in which "c" is the amount of starting olefinically unsaturated compound that has been converted into that certain compound and "d" is the total amount of starting olefinically unsaturated compound that has been converted.

It is a feature of the present invention that the catalytic system is very stable and has a long life—no plating out of metallic ruthenium has been observed. Replacement of ruthenium compound of component (a) with a palladium compound would result in plating out of metallic palladium.

DETAILED DESCRIPTION OF THE INVENTION

The compounds suitably utilized as the specified component (b) of the catalytic system for the process of this invention have a non-coordinating anion, by which is meant that little or no co-valent interaction takes place between the ruthenium compound and the anion. Component (b) preferably comprises a compound having an anion of sulphuric acid, of a sulphonic acid or of an acid that can be formed by interaction of a Lewis acid with a Broensted acid, which formation may take place in-situ in the carbonylation reaction mixture. Examples of such Lewis acids are $BF_3$, $AsF_5$, $SbF_5$, $PF_5$, $TaF_5$ and $NbF_5$ and examples of such Broensted acids are hydrohalogenic acids, in particular HF and HCl. Particularly preferred for use as component (b) is a compound which has an anion of trifluoromethanesulphonic acid [$CF_3SO_2(OH)$], of tetrafluoroboric acid ($HBF_4$) or of hexafluorophosphoric acid ($HPF_6$). Other examples of compounds suitable for use as component (b) of the catalytic system are compounds having an anion of perchloric acid ($HClO_4$), fluorosilicic acid ($H_2SiF_6$), fluorosulphonic acid [$SO_2(OH)F$] and chlorosulphonic acid [$SO_2(OH)Cl$].

The compound having a non-coordinating anion of an acid with a $pK_a$ below 0.5 may be a salt or an acid, and component (b) may suitably be a mixture of such a salt and such an acid. The salts used as component (b) may have a great variety of cations. Very good results have been obtained with cations of transition metals, particularly zinc and copper. Very good results have also been obtained with uranyl salts. In this respect, components (a) and (b) may be the same, i.e. when the ruthenium compound used as component (a) has the non-coordinating anion specified for the compound of component (b), as is the case with $Ru(PF_6)_3$.

The choice of a specific ruthenium compound for use as component (a) of the catalytic system is not critical to the invention. Examples of ruthenium compounds include ruthenium oxides and the aforementioned ruthenium salts of acids having a non-coordinating anion. Very good results have been obtained with ruthenium tris acetylacetonate.

The catalytically effective quantity of component (a) used in forming catalytic system for use in the invention may vary widely, but is generally in the range between $10^{-6}$ and $10^{-1}$, preferably between $10^{-5}$ and $10^{-2}$, gram-atom ruthenium per mol of starting olefinically unsaturated compound. Similarly the quantity of component (b) may also vary but is preferably in the range of from 0.1 to 100, more preferably from 0.5 to 20, equivalents per gram-atom of ruthenium.

The olefinically unsaturated compound, the CO, the water or alcohol, and the catalytic system are necessarily contacted at a temperature and pressure sufficient to effect the desired conversion to carboxylic acid or ester. Temperature and pressure are not narrowly critical to the reaction. The process is preferably carried out at a temperature in the range of from 100° C. to 250° C. and a pressure in the range of from 5 to 200 bar, but temperatures above or below said range or pressures above or below said range are suitable.

The olefinically unsaturated compound used as starting material in the invention may be an unsubstituted or a substituted alkene or cycloalkene, preferably one having 2-30, more preferably 2-20, carbon atoms and preferably 1-3 double bonds in the molecule. The alkene or cycloalkene may be substituted, for instance, with one or more halogen atoms or cyano, ester, alkoxy, hydroxy, carboxy or aryl groups. If the substituents are not inert under the reaction conditions, the carboxylation reaction may be accompanied with other reactions. For instance, the carbonylation of allyl alcohol is accompanied with esterification of the hydroxy group. Examples of specific olefinically unsaturated compounds suitable for use in the invention include ethene, propene, 1-butene, 2-butene, isobutene, the several isomeric pentenes, hexenes, octenes and dodecenes, cyclooctadiene-(1,5), cyclododecene, cyclododecatriene-(1,5,9), allyl alcohol, methyl acrylate, ethyl acrylate, methyl methacrylate, acrylonitrile, acrylamide, N,N-dimethylacrylamide, vinyl chloride, allyl chloride, acrolein, oleic acid, methyl allyl ether and styrene.

The alcohols suitably used in the process according to the invention may be aliphatic, cycloaliphatic or aromatic and may be substituted with one or more substituents, for instance the same substituents as mentioned hereinbefore in connection with substitution of the olefinically unsaturated starting compounds. The alcohol may therefore also be a phenol, including alkyl substituted phenol. The alcohols preferably contain not more than about 20 carbon atoms in the molecule. Examples of suitable alcohols include methanol, ethanol, propanol, isobutanol, tertiary butyl alcohol, stearyl alcohol, benzyl alcohol, cyclohexanol, allyl alcohol, chlorocapryl alcohol, ethylene glycol, 1,2-propanediol, 1,4-butanediol, glycerol, polyethylene glycol, 1,6-hexanediol, phenol and cresol.

Special preference is given to alkanols having in the range of from 1 to 10 carbons atoms per molecule. If the alcohol has more than one hydroxy group, different products may be formed, depending on the molar ratios existing between the reactive reagents. For instance, depending on the quantity of olefinically unsaturated compound used, either a mono-ester or a di-ester may be produced from glycerol.

If the process is carried out in the presence of water, the product is a carboxylic acid. If the process is carried out in the presence of an alcohol, the product is a carboxylic acid ester. The process may also suitably be carried out in the simultaneous presence of water and an alcohol, in which case a carboxylic acid and an ester are simultaneously formed. The process according to the present invention is particularly suitable for the preparation of methyl propionate, starting from ethylene, carbon monoxide and methanol. Methyl propionate is a valuable solvent.

In the process according to the invention the carbon monoxide may be used pure or diluted with an inert gas, such as nitrogen, noble gasses or carbon dioxide. The carbon monoxide containing gas may suitably contain hydrogen if the quantity of hydrogen present is relatively limited. For instance, it is generally preferred that the reaction mixture contain no more than about 10% v of hydrogen, and preference is further given to the use of carbon monoxide or a carbon monoxide-containing gas which contains less than about 5% v of hydrogen.

The molar ratio of the olefinically unsaturated compound to water or alcohol is not critical to the process of the invention. The molar ratio between the number of hydroxy groups and the number of olefinic double bonds is, for instance, suitably between 0.1:1 and 10:1. When using a mono-olefin and either water or a monohydric alcohol, preference is usually given to the use of an excess of the hydroxy compound mentioned, more preferably a molar ratio of hydroxy compound to olefin which is in the range from 1 to about 10. However, when using a polyhydric alcohol to prepare a polyester, it will generally be necessary to use an excess of olefinic compound.

The process according to the invention may be carried out batchwise, continuously or semi-continuously. Generally there is no need for the use of an added solvent since usually there will be an excess of one of the reactants—for instance the alcohol—which may serve as a solvent as well. If desired, however, an added solvent may be used, for instance dimethyl sulphoxide, diisopropyl sulphone, tetrahydrothiophene 1,1-dioxide (also referred to as sulfolane), acetone, chloroform, methyl isobutyl ketone, diglyme (dimethyl ether of di-ethylene glycol) or diisopropyl ether. The primary reaction product of the carbonylation reaction may also be used as a solvent.

The reaction mixtures obtained by carrying out the process of the invention may, if desired, be subjected to catalyst and product separation comprising one or more of such steps, for example, as stratification, solvent extraction, distillation, fractionation or adsorption. The catalytic system as well as unconverted starting compounds or solvent, if any, may be recycled in whole or in part to the reaction zone.

The catalytic system suitably utilized in the invention is a novel composition and is also considered an aspect of this invention.

The following Examples are intended to further illustrate the invention, without limiting its broader scope.

The experiments described in the examples were carried out in a 300 ml magnetically stirred Hastelloy C autoclave ("Hastelloy" is a trade mark). The reaction mixtures obtained were analyzed by means of gasliquid chromatography.

EXAMPLES 1–14

For each of Examples 1–14, the autoclave was charged with methanol (50 ml, 1.23 mol), ruthenium-(acetylacetonate)$_3$ (0.5 mmol) and a compound having an anion of an acid with a pK$_a$ below 0.5, flushed with carbon monoxide, sealed, charged with carbon monoxide until a partial pressure thereof of 25 bar was obtained, charged with ethylene until a partial pressure therof of 25 bar was obtained, and heated. After a reaction time of 5 hours the autoclave was allowed to cool to ambient temperature and opened for analysis of the reaction mixture.

Table 1 below identifies, for each of the Examples, the specific compound having an anion of an acid having a pK$_a$ below 0.5 which was used—referred to as "component (b)"—, the amount in which this compound was used, and the temperature to which the autoclave was heated. Table 1 also presents the reaction rates and the selectivities to carbonylation product (methyl propionate).

TABLE 1

| Example | Component (b) | mmol | Temperature °C. | Reaction rate, mol C$_2$H$_4$ per gram - atom Ru per hour | Selectivity, % to methyl propionate |
|---|---|---|---|---|---|
| 1 | UO$_2$SO$_4$ | 1 | 150 | 20 | 92 |
| 2 | " | 1 | 160 | 35 | 93 |
| 3 | " | 1 | 180 | 100 | 92 |
| 4 | ZnSO$_4$ | 1 | 160 | 20 | 94 |
| 5 | CuSO$_4$ | 1 | 160 | 20 | 92 |
| 6 | H$_2$SO$_4$ | 2 | 150 | 15 | 76 |
| 7 | Zr(SO$_4$)$_2$ | 1 | 150 | 10 | 75 |
| 8 | Cu(BF$_4$)$_2$ | 1 | 160 | 20 | 93 |

TABLE 1-continued

| Example | Component (b) | mmol | Temperature °C. | Reaction rate, mol C$_2$H$_4$ per gram-atom Ru per hour | Selectivity, % to methyl propionate |
| --- | --- | --- | --- | --- | --- |
| 9 | " | 1 | 175 | 50 | 92 |
| 10 | HBF$_4$ | 1 | 175 | 40 | 97 |
| 11 | HPF$_6$ | 1 | 175 | 80 | 93 |
| 12 | " | 2 | 175 | 100 | 93 |
| 13 | Cu(PF$_6$)$_2$ | 2 | 175 | 120 | 94 |
| 14 | CF$_3$SO$_3$H | 2 | 150 | 10 | 85 |

COMPARATIVE EXPERIMENTS A–C

These three experiments were carried out as described in Examples 1–14 with the exception of the replacement of the component (b) identified in Table 1 with another compound having an anion of an acid with a pK$_a$ above 0.5. The replacement compound and the reaction temperature for each of the experiment are shown in Table 2. The selectivities to methyl propionate found in these experiments were considerably lower than these presented in Table 1, illustrating the criticality of the use as component (b) of a compound having an anion of an acid with a pK$_a$ below 0.5.

TABLE 2

| Comparative Experiment | Additional Component | mmol | Temperature °C. | Reaction rate, mol C$_2$H$_4$ per gram-atom Ru per hour | Selectivity, % to methyl propionate |
| --- | --- | --- | --- | --- | --- |
| A | p-toluenesulphonic acid | 2 | 150 | 10 | 65 |
| B | cupric(tosylate)$_2$ | 1 | 150 | 15 | 50 |
| C | " | 1 | 175 | 50 | 60 |

COMPARATIVE EXPERIMENT D

Example 1 was repeated with the difference that no UO$_2$SO$_4$ was present. No reaction was observed.

EXAMPLE 15

Example 8 was repeated with the difference that, in this Example 15, 0.5 mmol of a ligand, in particular 1,3-di(diphenylphosphino)propane, was added to the process mixture. The reaction rate was 15 mol ethylene per gram-atom ruthenium per hour and the selectivity to methyl propionate was 81%. Comparison with the results of Example 8 shows that reaction rate and selectivity are higher in the absence of 1,3-di(diphenylphosphino)propane.

EXAMPLE 16

The autoclave was charged with methanol (50 ml), ruthenium(acetylacetonate)$_3$ (0.5 mmol) and cupric hexafluorophosphate (2 mmol), flushed with carbon monoxide, sealed, charged with carbon monoxide until a partial pressure thereof of 40 bar was obtained, charged with propylene (30 ml) and heated to a temperature of 175° C. After a reaction time of 5 hours the autoclave was allowed to cool to ambient temperature and was opened for analysis of the reaction mixture.

The reaction rate was 40 mol propylene per gram-atom ruthenium per hour and the selectivity to the total of methyl butyrate and methyl isobutyrate was 96% in a ratio of 58:42, respectively.

EXAMPLE 17

The autoclave was charged with diglyme (40 mol), ruthenium(acetylacetonate)$_3$ (0.5 mmol), hexafluorophosphoric acid (1.5 mmol) and water (10 ml), flushed with carbon monoxide, sealed, charged with carbon monoxide until a partial pressure thereof of 25 bar was obtained, charged with ethylene until a partial pressure thereof of 25 bar was obtained and heated to a temperature of 160° C. After a reaction time of 5 hours the autoclave was allowed to cool to ambient temperature and was opened for analysis of the reaction mixture.

The reaction rate was 65 mol ethylene per gram-atom ruthenium per hour and the selectivity to propionic acid was 95%.

EXAMPLE 18

The autoclave was charged with water (50 ml), ruthenium(acetylacetonate)$_3$ (0.5 mmol) and cupric hexafluorophosphate (2 mmol), flushed with carbon monoxide, sealed, charged with carbon monoxide until a partial pressure thereof of 25 bar was obtained, charged with ethylene until a partial pressure thereof of 25 bar was obtained, and heated to a temperature of 160° C. After a reaction time of 5 hours, the autoclave was allowed to cool to ambient temperature and was opened for analysis of the reaction mixture.

The reaction rate was 40 mol ethylene per gram-atom ruthenium per hour and the selectivity to propionic acid was 90%.

This example shows that water may be used as a solvent.

I claim as my invention:

1. A composition consisting essentially of the following components:
   component (a)—a ruthenium compound, and
   component (b)—a salt having a non-coordinating anion of an acid with a pK$_a$, measured at 25° C. in aqueous solution, below 0.5,
   component (a) not being the same as component (b).

2. The composition of claim 1, wherein component (b) is a salt of a transition metal selected from the group consisting of zinc and copper, having an anion selected from the group consisting of anions of trifluoromethanesulphonic acid, of tetrafluoroboric acid, and of hexafluorophosphoric acid.

3. The composition of claim 2, wherein component (a) comprises ruthenium tris acetylacetonate.

* * * * *